United States Patent
Fernandez-Prieto et al.

(10) Patent No.: US 9,534,191 B2
(45) Date of Patent: *Jan. 3, 2017

(54) STRUCTURED LIQUID COMPOSITIONS

(71) Applicant: The Procter & Gamble Company, Cincinnati, OH (US)

(72) Inventors: Susana Fernandez-Prieto, Benicarlo (ES); Neil Joseph Lant, Newcastle upon Tyne (GB); Vincenzo Guida, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,603

(22) Filed: Jul. 10, 2014

(65) Prior Publication Data
US 2015/0159120 A1 Jun. 11, 2015

(30) Foreign Application Priority Data

Dec. 7, 2013 (EP) .................................... 13176301

(51) Int. Cl.
| | |
|---|---|
| *C11D 1/00* | (2006.01) |
| *C11D 3/22* | (2006.01) |
| *C11D 3/37* | (2006.01) |
| *C11D 3/382* | (2006.01) |
| *C11D 3/386* | (2006.01) |
| *C12N 9/32* | (2006.01) |
| *C12N 9/42* | (2006.01) |
| *C12N 9/24* | (2006.01) |

(52) U.S. Cl.
CPC ........... *C11D 3/222* (2013.01); *C11D 3/38636* (2013.01); *C11D 3/38645* (2013.01); *C12N 9/2422* (2013.01); *C12N 9/2434* (2013.01); *C12N 9/2437* (2013.01); *C12N 9/2491* (2013.01); *C12Y 302/01004* (2013.01); *C12Y 302/01151* (2013.01)

(58) Field of Classification Search
CPC ............... C11D 1/00; C11D 3/22; C11D 3/37; C11D 3/382; C11D 3/386; C11D 7/268; C11D 9/262

See application file for complete search history.

(56) References Cited

U.S. PATENT DOCUMENTS

| | | |
|---|---|---|
| 4,481,076 A | 11/1984 | Herrick et al. |
| 5,964,983 A | 10/1999 | Dinand et al. |
| 5,998,349 A | 12/1999 | Guillou |
| 2008/0108714 A1* | 5/2008 | Swazey ................. A61K 8/027 516/31 |
| 2008/0146485 A1 | 6/2008 | Swazey et al. |
| 2012/0071383 A1 | 3/2012 | Perez-Prat et al. |
| 2012/0225804 A1 | 9/2012 | D'Ambrogio et al. |
| 2013/0025500 A1 | 1/2013 | Jones et al. |
| 2013/0029894 A1* | 1/2013 | Bettiol ................. C11D 3/1266 510/236 |
| 2013/0029895 A1 | 1/2013 | Bettiol et al. |

FOREIGN PATENT DOCUMENTS

| | | | |
|---|---|---|---|
| EP | 0295865 A2 | | 12/1988 |
| WO | WO 2009/135765 A1 | | 11/2009 |
| WO | WO 2011/054389 | * | 5/2011 |
| WO | WO 2011/054389 A1 | | 5/2011 |

OTHER PUBLICATIONS

EP Search Report; Dated Oct. 22, 2013; 8 Pages.
U.S. Appl. No. 14/327,608, filed Jul. 10, 2014, Fernandez-Prieto, et al.
Istva'n Siro' and David Placket, Microfibrillated cellulose and new nanocomposite materials: a review, Received: Sep. 11, 2009 / Accepted: Jan. 29, 2010 / Published online. Feb. 21, 2010 _Springer Science+Business Media B.V. 2010, pp. 459-494.

* cited by examiner

*Primary Examiner* — Brian P Mruk
(74) *Attorney, Agent, or Firm* — Gregory S. Darley-Emerson; Leonard W Lewis; Steven W Miller

(57) ABSTRACT

Microfibrillated cellulose, derived from vegetables or wood, can be used to provide a liquid composition which is compatible with a broad range of ingredients suitable for consumer applications, including enzymes, while still providing good structuring of the liquid composition, without affecting ease of pour.

17 Claims, No Drawings

STRUCTURED LIQUID COMPOSITIONS

FIELD OF THE INVENTION

Microfibrillated cellulose, derived from vegetables or wood, are compatible with a wide variety of typical consumer product ingredients, while also providing improved stability of soluble and insoluble materials in liquid compositions.

BACKGROUND OF THE INVENTION

It has long been desired to create a broad range of variants, offering unique benefits, from a single base liquid composition. By adding specific benefit agents to such a base, one could simply and cost-effectively provide consumer product compositions that are tailored to a specific group of users. However, a major challenge is to structure such compositions, using an external structurant which is compatible with a broad range of potential consumer product ingredients.

Various external structurants, for providing rheological benefits to liquid compositions, are known. Examples of desired benefits of such structurants include particle suspension, shear thinning properties, a thick appearance on the shelf, as well as stabilization of soluble and insoluble ingredients which are desired to be incorporated within the composition. Known external structurants include those derived from castor oil, fatty acids, fatty esters, or fatty soap water-insoluble waxes. However, their applicability for liquid compositions is limited due to degradation by conventional consumer composition ingredients such as enzymes, including lipase, cellulase, and the like. Polymeric structurants have also been used in such liquid compositions. However, they can result in a stringy pour profile that is undesirable to the consumer, particularly when "gel-like" viscosities are desired. Moreover, cellulose-based polymeric structurants are susceptible to various enzymes, such as cellulases.

As such, a need remains for a structurant that is compatible with a broad range of consumer liquid composition ingredients, including enzymes, while still providing good structuring of the detergent ingredients and being easy to pour.

A bacterial cellulose with a reticulated structure is known. Liquid compositions that are structured using citrus fibres are known. Processes for preparing liquid compositions which comprise microfibrous cellulose are known. Microfibrillated celluloses, and methods for preparing them, are also known.

SUMMARY OF THE INVENTION

The present invention relates to a liquid composition comprising: surfactant, and microfibrillated cellulose derived from vegetables or wood.

The present invention further relates to a process to manufacture a liquid composition comprising a surfactant and microfibrillated cellulose derived from vegetables or wood, the process comprising the steps of: providing a structuring premix comprising microfibrillated cellulose, derived from vegetables or wood; and incorporating the structuring premix into a liquid premix using high shear mixing.

DETAILED DESCRIPTION OF THE INVENTION

Microfibrillated cellulose, derived from vegetables or wood, has been found to provide structuring to surfactant-containing liquid compositions. Such microfibrillated cellulose are compatible with a broad range of typical consumer product ingredients, including detersive enzymes, while still providing a combination of good structuring and ease of pouring. In addition to not being degraded by detersive enzymes, there structuring capability is resilient to the addition of typical adjunct ingredients, added at levels which are suitable for liquid compositions, particularly for use consumer product applications.

Liquid compositions, which are structured using microfibrillated cellulose derived from vegetables or wood, have a high low-shear viscosity. Thus, microfibrillated cellulose, derived from vegetables or wood, is also effective at suspending particulates or droplets in liquid compositions, including solid particulates such as perfume microcapsules, and the like, and liquid droplets such as perfume droplets, other oils, and the like.

Unless otherwise noted, all component or composition levels are in reference to the active portion of that component or composition, and are exclusive of impurities, for example, residual solvents or by-products, which may be present in commercially available sources of such components or compositions.

As defined herein, "essentially free of" a component means that the component is present at a level of less that 15%, preferably less 10%, more preferably less than 5%, even more preferably less than 2% by weight of the respective premix or composition. Most preferably, "essentially free of" a component means that no amount of that component is present in the respective premix, or composition.

As defined herein, "stable" means that no visible phase separation is observed for a liquid composition kept at 25° C. for a period of at least two weeks, preferably at least four weeks, more preferably at least a month or even more preferably at least four months, as measured using the Floc Formation Test, described in USPA 2008/0263780 A1.

All percentages, ratios and proportions used herein are by weight percent of the respective premix or composition, unless otherwise specified. All average values are calculated "by weight" of the respective premix, composition, or components thereof, unless otherwise expressly indicated.

Unless otherwise noted, all component, premix, or composition levels are in reference to the active portion of that component, premix, or composition, and are exclusive of impurities, for example, residual solvents or by-products, which may be present in commercially available sources of such components or compositions.

All measurements are performed at 25° C. unless otherwise specified.

Microfibrillated Cellulose Derived from Vegetables or Wood:

External structurants provide a structuring benefit independently from, or extrinsic from, any structuring effect of surfactants in the composition. For instance, the external structurant can impart a shear thinning viscosity profile to a liquid composition, independently from, or extrinsic from, any structuring effect of the detersive surfactants of the composition.

Microfibrillated cellulose, derived from vegetables or wood, has been found to be suitable for use as an external structurant, for liquids comprising at least one surfactant. Suitable vegetables, from which the microfibrillated cellulose can be derived, include: sugar beet, chicory root, potato, carrot, and the like. Preferred vegetables or wood can be selected from the group consisting of: sugar beet, chicory root, and mixtures thereof.

Vegetable and wood fibres comprise a higher proportion of insoluble fibre than fibres derived from fruits, including citrus fruits. Preferred microfibrillated cellulose are derived from vegetables and woods which comprise less than 10% soluble fibre as a percentage of total fibre.

Suitable processes for deriving microfibrillated cellulose from vegetables and wood include the process described in U.S. Pat. No. 5,964,983.

Microfibrillated cellulose (MFC), is a material composed of nanosized cellulose fibrils, typically having a high aspect ratio (ratio of length to cross dimension). Typical lateral dimensions are 1 to 100, or 5 to 20 nanometers, and longitudinal dimension is in a wide range from nanometers to several microns. For improved structuring, the microfibrillated cellulose preferably has an average aspect ratio (l/d) of from 50 to 200,000, more preferably from 100 to 10,000.

Sugar beet pulp (SBP) is a by-product from the beet sugar industry. On a dry weight basis, SBP typically contains 65-80% polysaccharides, consisting roughly of 40% cellulose, 30% hemicelluloses, and 30% pectin.

Chicory (*Cichorium intybus* L.) belongs to the Asteraceae family and is a biennial plant with many applications in the food industry: the dried and roasted roots are used for flavouring coffee; the young leaves can be added to salads and vegetable dishes, and chicory extracts are used for foods, beverages and the like. Chicory fibres, present in chicory root, are known to comprise pectine, cellulose, hemicelluloses, and inulin. Inulin is a polysaccharide which is composed of a chain of fructose units with a terminal glucose unit. Chicory roots are particularly preferred as a source of inulin, since they can be used for the production of inulin which comprises long glucose and fructose chains. Chicory fibres, used to make the microfibrillated cellulose, can be derived as a by-product during the extraction of inulin. After the extraction of the inulin, chicory fibres typically form much of the remaining residue.

The fibres derived from sugar beet pulp and chicory comprise hemicelluloses. Hemicelluloses typically have a structure which comprises a group of branched chain compounds with the main chain composed of alpha-1,5-linked 1-arabinose and the side chain by alpha-1,3-linked 1-arabinose. Besides arabinose and galactose, the hemicelluloses also contained xylose and glucose. Before use for structuring purposes, the fibres can be ezymatically treated to reduce branching.

Microfibrils, derived from vegetables or wood, include a large proportion of primary wall cellulose, also called parenchymal cell cellulose (PCC). It is believed that such microfibrils formed from such primary wall cellulose provide improved structuring. In addition, microfibrils in primary wall cellulose are deposited in a disorganized fashion, and are easy to dissociate and separate from the remaining cell residues via mechanical means.

Charged groups can also be introduced into the microfiber cellulose, for instance, via carboxymethylation, as described in Langmuir 24 (3), pages 784 to 795. Carboxymethylation results in highly charged microfibillated cellulose which is easier to liberate from the cell residues during making, and have modified structuring benefits.

The microfibrillated cellulose can be derived from vegetables or wood which has been pulped and undergone a mechanical treatment comprising a step of high intensity mixing in water, until the vegetable or wood has consequently absorbed at least 15 times its own dry weight of water, preferably at least 20 times its own dry weight, in order to swell it. It may be derived by an environmentally friendly process from a sugar beet or chicory root waste stream. This makes it more sustainable than prior art external structurants.

Furthermore, it requires no additional chemicals to aid its dispersal and it can be made as a structuring premix to allow process flexibility.

The process to make microfibrillated cellulose derived from vegetables or wood, particularly from sugar beet or chicory root, is also simpler and less expensive than that for bacterial cellulose.

Microfibrillated cellulose, derived from vegetables or wood, can be derived using any suitable process, such as the process described in U.S. Pat. No. 5,964,983. For instance, the raw material, such as sugar beet or chicory root, can first be pulped, before being partially hydrolysed, using either acid or basic hydrolysis, to extract the pectins and hemicelluloses. The solid residue can then be recovered from the suspension, and a second extraction under alkaline hydrolysis conditions can be carried out, before recovering the cellulosic material residue by separating the suspension after the second extraction. The one or more hydrolysis steps are typically done at a temperature of from 60° C. to 100° C., more typically at from 70° C. to 95° C., with at least one of the hydrolysis steps being preferably under basic conditions. Caustic soda, potash, and mixtures thereof, is typically used at a level of less than 9 wt %, more preferably from 1% to 6% by weight of the mixture, for basic hydrolysis. The residues are then typically washed and optionally bleached to reduce or remove colouration. The residue is then typically made into an aqueous suspension, usually comprising 2 to 10 wt % solid matter, which is then homogenised. Homogenisation can be done using any suitable equipment, and can be carried out by mixing or grinding or any other high mechanical shear operation, typically followed by passing the suspension through a small diameter orifice and preferably subjecting the suspension to a pressure drop of at least 20 MPa and to a high velocity shearing action followed by a high velocity decelerating impact.

Liquid compositions, comprising microfibrillated cellulose derived from vegetables or wood, are typically thixotropic, providing good suspension of particles and droplets, while easily flowing under shear. As a result, microfibrillated cellulose, derived from vegetables or wood, is a particularly suitable structurant for surfactant containing liquid compositions, since it stabilises suspended insoluble material in the liquid composition, while reducing phase separation, and being compatible with a wide variety of typical adjuncts, including enzymes. Moreover, such microfibrillated cellulose, derived from vegetables or wood, are believed to also improve deposition of actives, including perfumes, perfume microcapsules, and the like.

Liquid Compositions Comprising Microfibrillated Cellulose Derived from Vegetables or Wood:

The liquid compositions of the present invention typically comprise from 0.05 to 10 wt %, preferably from 0.1 to 5 wt %, more preferably from 0.15 to 2 wt % of the microfibrillated cellulose, derived from vegetables or wood.

Suitable liquid compositions include consumer products such as: products for treating fabrics, including laundry detergent compositions, and rinse additives such as fabric softeners; hard surface cleaners including dishwashing compositions, floor cleaners, and toilet bowl cleaners. Such liquid compositions may provide a cleaning benefit, and hence can comprise detersive surfactant, so as to provide a noticeable cleaning benefit. Most preferred are liquid laundry detergent compositions, which are capable of cleaning a fabric, such as in a domestic washing machine.

As used herein, "liquid composition" refers to any composition comprising a liquid capable of wetting and treating a substrate, such as fabric or hard surface. Liquid compositions are more readily dispersible, and can more uniformly coat the surface to be treated, without the need to first dissolve the composition, as is the case with solid compositions. Liquid compositions can flow at 25° C., and include compositions that have an almost water like viscosity, but also include "gel" compositions that flow slowly and hold their shape for several seconds or even minutes.

A suitable liquid composition can include solids or gases in suitably subdivided form, but the overall composition excludes product forms which are non-liquid overall, such as tablets or granules. The liquid compositions preferably have densities in the range from of 0.9 to 1.3 grams per cubic centimeter, more preferably from 1.00 to 1.10 grams per cubic centimeter, excluding any solid additives but including any bubbles, if present.

Preferably, the liquid composition comprises from 1% to 95% by weight of water, non-aminofunctional organic solvent, and mixtures thereof. For concentrated liquid compositions, the composition preferably comprises from 15% to 70%, more preferably from 20% to 50%, most preferably from 25% to 45% by weight of water, non-aminofunctional organic solvent, and mixtures thereof. Alternatively, the liquid composition may be a low water liquid composition. Such low water liquid compositions can comprise less than 20%, preferably less than 15%, more preferably less than 10% by weight of water.

The liquid composition of the present invention may comprise from 2% to 40%, more preferably from 5% to 25% by weight of a non-aminofunctional organic solvent.

The liquid composition can also be encapsulated in a water soluble film, to form a unit dose article. Such unit dose articles comprise a liquid composition of the present invention, wherein the liquid composition is a low water liquid composition, and the liquid composition is enclosed in a water-soluble or dispersible film.

The unit dose article may comprise one compartment, formed by the water-soluble film which fully encloses at least one inner volume, the inner volume comprising the low water liquid composition. The unit dose article may optionally comprise additional compartments comprising further low water liquid compositions, or solid compositions. A multi-compartment unit dose form may be desirable for such reasons as: separating chemically incompatible ingredients; or where it is desirable for a portion of the ingredients to be released into the wash earlier or later. The unit-dose articles can be formed using any means known in the art.

Unit dose articles, wherein the low water liquid composition is a liquid laundry detergent composition are particularly preferred.

Suitable water soluble pouch materials include polymers, copolymers or derivatives thereof. Preferred polymers, copolymers or derivatives thereof are selected from the group consisting of: polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof.

The liquid compositions of the present invention may comprise from 0.5 to 40 wt %, preferably from 2 to 35 wt %, more preferably from 10 to 30 wt % of the surfactant.

The liquid composition comprises a surfactant selected from the group consisting of: anionic surfactant, nonionic surfactant, cationic surfactant, and mixtures thereof.

The liquid compositions can provide a detergency benefit. Such liquid detergent compositions typically comprise a surfactant selected from the group consisting of: anionic surfactant, nonionic surfactant, and mixtures thereof.

For liquid compositions which provide a detersive benefit, the preferred weight ratio of anionic to nonionic surfactant is from 100:0 (i.e. no nonionic surfactant) to 5:95, more preferably from 99:1 to 1:4, most preferably from 5:1 to 1.5:1.

The liquid detergent compositions of the present invention preferably comprise from 1 to 50%, more preferably from 5 to 40%, most preferably from 10 to 30% by weight of one or more anionic surfactants. Preferred anionic surfactant are selected from the group consisting of: C11-C18 alkyl benzene sulphonates, C10-C20 branched-chain and random alkyl sulphates, C10-C18 alkyl ethoxy sulphates, mid-chain branched alkyl sulphates, mid-chain branched alkyl alkoxy sulphates, C10-C18 alkyl alkoxy carboxylates comprising 1-5 ethoxy units, modified alkylbenzene sulphonate, C12-C20 methyl ester sulphonate, C10-C18 alpha-olefin sulphonate, C6-C20 sulphosuccinates, and mixtures thereof. However, by nature, every anionic surfactant known in the art of detergent compositions may be used, such as those disclosed in "Surfactant Science Series", Vol. 7, edited by W. M. Linfield, Marcel Dekker. The detergent compositions preferably comprise at least one sulphonic acid surfactant, such as a linear alkyl benzene sulphonic acid, or the water-soluble salt form of the acid.

The liquid compositions of the present invention preferably comprise up to 30%, more preferably from 1 to 15%, most preferably from 2 to 10% by weight of one or more nonionic surfactants. Suitable nonionic surfactants include, but are not limited to C12-C18 alkyl ethoxylates ("AE") including the so-called narrow peaked alkyl ethoxylates, C6-C12 alkyl phenol alkoxylates (especially ethoxylates and mixed ethoxy/propoxy), block alkylene oxide condensate of C6-C12 alkyl phenols, alkylene oxide condensates of C8-C22 alkanols and ethylene oxide/propylene oxide block polymers (Pluronic®-BASF Corp.), as well as semi polar nonionics (e.g., amine oxides and phosphine oxides). An extensive disclosure of suitable nonionic surfactants can be found in U.S. Pat. No. 3,929,678.

The liquid composition may also include conventional detergent ingredients selected from the group consisting of: additional surfactants selected from amphoteric, zwitterionic, cationic surfactant, and mixtures thereof; enzymes; enzyme stabilizers; amphiphilic alkoxylated grease cleaning polymers; clay soil cleaning polymers; soil release polymers; soil suspending polymers; bleaching systems; optical brighteners; hueing dyes; particulates; perfume and other odour control agents, including perfume delivery systems; hydrotropes; suds suppressors; fabric care perfumes; pH adjusting agents; dye transfer inhibiting agents; preservatives; non-fabric substantive dyes; and mixtures thereof.

Microfibrillated cellulose, derived from vegetables or wood, is particularly effective at stabilizing suspended insoluble material since it provides the liquid composition with a thixotropic rheology profile, and a yield stress which is sufficiently high enough to suspend such insoluble material. The composition preferably comprises sufficient microfibrillated cellulose to provide a yield stress of greater than 0.005 Pa, preferably from 0.01 to 1 Pa, more preferably from 0.1 to 1 Pa. As such, the aqueous structuring premixes of the present invention are particularly suited for stabilizing liquid compositions which further comprise suspended insoluble material. Suitable suspended insoluble material can be selected from the group consisting of: particulates, insoluble fluids, and mixtures thereof. Suspended insoluble materials are those which have a solubility in the liquid composition of less than 1%, at a temperature of 21° C.

The particulates may be microcapsules such as perfume encapsulates, or care additives in encapsulated form. The particulates may alternatively, or additionally, take the form of insoluble ingredients such as quaternary ammonium materials, insoluble polymers, insoluble optical brighteners, enzymes, and other known benefit agents found, for example, in EP1328616. The amount of particulates may be from 0.001 to up to 10 or even 20 wt %.

Microcapsules are typically added to liquid compositions, in order to provide a long lasting in-use benefit to the treated substrate. Microcapsules can be added at a level of from 0.01% to 10%, more preferably from 0.1% to 2%, even more preferably from 0.15% to 0.75% of the encapsulated active, by weight of the liquid composition. In a preferred embodiment, the microcapsules are perfume microcapsules, in which the encapsulated active is a perfume. Such perfume microcapsules release the encapsulated perfume upon breakage, for instance, when the treated substrate is rubbed.

The term "microcapsule" is used herein in the broadest sense to include a core that is encapsulated by the microcapsule wall. In turn, the core comprises a benefit agent, such as a perfume. The microcapsules typically comprise a microcapsule core and a microcapsule wall that surrounds the microcapsule core. The microcapsule wall is typically formed by cross-linking formaldehyde with at least one other monomer.

The microcapsule core may optionally comprise a diluent. Diluents are material used to dilute the benefit agent that is to be encapsulated, and are hence preferably inert. That is, the diluent does not react with the benefit agent during making or use. Preferred diluents may be selected from the group consisting of: isopropylmyristate, propylene glycol, poly(ethylene glycol), or mixtures thereof.

Microcapsules, and methods of making them are disclosed in the following references: US 2003-215417 A1; US 2003-216488 A1; US 2003-158344 A1; US 2003-165692 A1; US 2004-071742 A1; US 2004-071746 A1; US 2004-072719 A1; US 2004-072720 A1; EP 1393706 A1; US 2003-203829 A1; US 2003-195133 A1; US 2004-087477 A1; US 2004-0106536 A1; U.S. Pat. No. 6,645,479; U.S. Pat. No. 6,200,949; U.S. Pat. No. 4,882,220; U.S. Pat. No. 4,917,920; U.S. Pat. No. 4,514,461; U.S. RE 32713; U.S. Pat. No. 4,234,627.

Encapsulation techniques are disclosed in MICROENCAPSULATION: Methods and Industrial Applications, Edited by Benita and Simon (Marcel Dekker, Inc., 1996). Formaldehyde based resins such as melamine-formaldehyde or urea-formaldehyde resins are especially attractive for perfume encapsulation due to their wide availability and reasonable cost.

The microcapsules preferably have a size of from 1 micron to 75 microns, more preferably from 5 microns to 30 microns. The microcapsule walls preferably have a thickness of from 0.05 microns to 10 microns, more preferably from 0.05 microns to 1 micron. Typically, the microcapsule core comprises from 50% to 95% by weight of the benefit agent.

The liquid composition may optionally comprise a suspended insoluble fluid. Suitable insoluble fluids include silicones, perfume oils, and the like. Perfume oils provide an odour benefit to the liquid composition, or to substrates treated with the liquid composition. When added, such perfumes are added at a level of from 0.1% to 5%, more preferably from 0.3% to 3%, even more preferably from 0.6% to 2% by weight of the liquid composition. Suitable silicones include silicones which provide an anti-foam benefit, a fabric softening benefit, and combinations thereof. For improved anti-foaming or fabric softening, the silicones can be functionalised, including amino-functionalised.

Microfibrillated cellulose, derived from vegetables or wood, particularly derived from sugar beet or chicory root, is surprisingly resistant to degradation by: cellulases, endoglucanase with activity towards xyloglucan, and mixtures thereof. Hence, the liquid composition can comprise at least one enzyme selected from the group consisting of: cellulases, endoglucanase with activity towards xyloglucan, and mixtures thereof.

Suitable cellulases include endo-beta-1,4-glucanases, cellobiohydrolases and beta-1,4-glucosidases, of bacterial or fungal origin, from any family of glycosyl hydrolase exhibiting cellulase activity. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, and WO 98/12307.

Commercially available cellulases include Celluzyme®, and Carezyme® (Novozymes A/S), Clazinase®, Puradax® EG-L and Puradax® HA (Genencor International Inc.), and KAC®-500(B) (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403) and mixtures thereof. Suitable endoglucanases are sold under the tradenames Celluclean® and Whitezyme® (Novozymes A/S, Bagsvaerd, Denmark). Whitezyme® is an example of an endoglucanase exhibiting activity towards both cellulose and xyloglucan, and is a variant of a Glycosyl Hydrolase family 44 endoglucanase truncated from an assembly endogenous to *Paenibacillus polyxyma*.

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany). The cellulase may be intentionally formulated, or it may be introduced to the detergent composition as an impurity in another raw material, especially an enzyme. Commercial enzymes of many classes, for example protease, alpha-amylase, beta-mannanase, pectate lyase and lipase, may contain additional cellulase activity as a result of the production microorganism expressing cellulase enzymes that are not fully removed during the purification steps, or through contamination from other products during the enzyme production process. The commercial protease Purafect® Prime (Genencor Division of Danisco) is an example of a non-cellulase enzyme which typically contains significant cellulase impurities.

Another source of non-intentional presence of cellulase in detergent compositions is from cross-contamination in production plants, for example when changing over from a cellulase-containing formula to one with no intentionally formulated cellulase.

The liquid compositions of the present invention may comprise from 0.0001% to 8% by weight of other detersive enzymes which provide improved cleaning performance and/or fabric care benefits. Such compositions preferably have a composition pH of from 6 to 10.5. Suitable enzymes can be selected from the group consisting of: lipase, protease, amylase, mannanase, pectate lyase, xyloglucanase, and mixtures thereof, in addition to the cellulase enzyme. A preferred enzyme combination comprises a cocktail of conventional detersive enzymes such as lipase, protease, and amylase. Detersive enzymes are described in greater detail in U.S. Pat. No. 6,579,839.

Microfibrillated cellulose, derived vegetables or wood, particularly from sugar beet or chicory root are effective at preventing the segregation of water-soluble polymers, and any resultant phase separation of the liquid composition. Hence, the liquid composition of the present invention may comprise a water-soluble polymer. Water soluble are soluble or dispersible to at least the extent of 0.01% by weight in distilled water at 25° C. The liquid composition may comprise one or more water soluble polymers.

Suitable polymers include carboxylate polymers, polyethylene glycol polymers, polyester soil release polymers such as terephthalate polymers, amine polymers, cellulosic polymers, dye transfer inhibition polymers, dye lock polymers such as a condensation oligomer produced by condensation of imidazole and epichlorhydrin, optionally in ratio of 1:4:1, hexamethylenediamine derivative polymers, and any combination thereof.

Suitable carboxylate polymers include maleate/acrylate random copolymer or polyacrylate homopolymer. The carboxylate polymer may be a polyacrylate homopolymer having a molecular weight of from 4,000 Da to 9,000 Da, or from 6,000 Da to 9,000 Da. Other suitable carboxylate polymers are co-polymers of maleic acid and acrylic acid, and may have a molecular weight in the range of from 4,000 Da to 90,000 Da.

Other suitable carboxylate polymers are co-polymers comprising: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

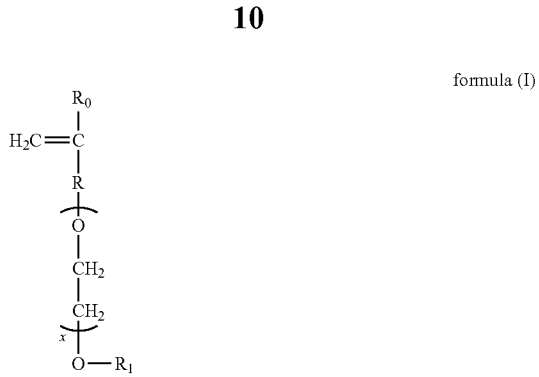

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or $C_1$ to $C_{20}$ organic group;

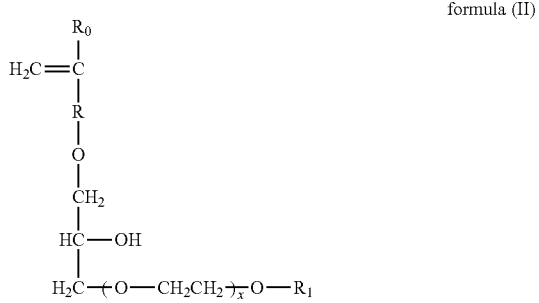

formula (II)

in formula (II), $R_0$ represents a hydrogen atom or $CH_3$ group, R represents a $CH_2$ group, $CH_2CH_2$ group or single bond, X represents a number 0-5, and $R_1$ is a hydrogen atom or $C_1$ to $C_{20}$ organic group.

Suitable polyethylene glycol polymers include random graft co-polymers comprising: (i) hydrophilic backbone comprising polyethylene glycol; and (ii) hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22.

Suitable polyester soil release polymers have a structure as defined by one of the following structures (I), (II) or (III):

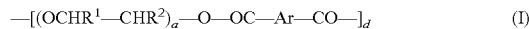

(I)

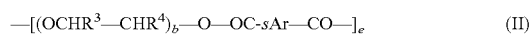

(II)

(III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is H, Na, Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or any mixture thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group. Suitable polyester soil release polymers are terephthalate polymers having the structure of formula (I) or (II) above.

Suitable polyester soil release polymers include the Repel-o-tex series of polymers such as Repel-o-tex SF2 (Rhodia) and/or the Texcare series of polymers such as Texcare SRA300 (Clariant).

Suitable amine polymers include polyethylene imine polymers, such as alkoxylated polyalkyleneimines, optionally comprising a polyethylene and/or polypropylene oxide block.

The composition can comprise cellulosic polymers, such as polymers selected from alkyl cellulose, alkyl alkoxyalkyl cellulose, carboxyalkyl cellulose, alkyl carboxyalkyl, and any combination thereof. Suitable cellulosic polymers are selected from carboxymethyl cellulose, methyl cellulose, methyl hydroxyethyl cellulose, methyl carboxymethyl cellulose, and mixtures thereof. The carboxymethyl cellulose can have a degree of carboxymethyl substitution from 0.5 to 0.9 and a molecular weight from 100,000 Da to 300,000 Da. Another suitable cellulosic polymer is hydrophobically modified carboxymethyl cellulose, such as Finnfix SH-1 (CP Kelco). Other suitable cellulosic polymers may have a degree of substitution (DS) of from 0.01 to 0.99 and a degree of blockiness (DB) such that either DS+DB is of at least 1.00 or DB+2DS−$DS^2$ is at least 1.20. The substituted cellulosic polymer can have a degree of substitution (DS) of at least 0.55. The substituted cellulosic polymer can have a degree of blockiness (DB) of at least 0.35. The substituted cellulosic polymer can have a DS+DB, of from 1.05 to 2.00. A suitable substituted cellulosic polymer is carboxymethylcellulose.

Another suitable cellulosic polymer is cationically modified hydroxyethyl cellulose.

The laundry detergent compositions may comprise one or more dye transfer inhibition (DTI) polymers. Suitable DTIs include polyamine N-oxide polymers, copolymers of N-vinylpyrrolidone and N-vinylimidazole, polyvinylpyrrolidone polymers, polyvinyloxazolidones and polyvinylimidazoles or mixtures thereof. The DTI polymers discussed above are well known in the art and commercially available, for example PVP-K15 and K30 (Ashland), Sokalan HP165, HP50, HP53, HP59, HP56K, HP56, HP66 (BASF), Chromabond S-400, 5403E and S-100 (Ashland), and Polyquart FDI (Cognis).

Suitable polymers include hexamethylenediamine derivative polymers, typically having the formula:

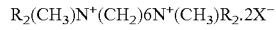

wherein $X^-$ is a suitable counter-ion, for example chloride, and R is a poly(ethylene glycol) chain having an average degree of ethoxylation of from 20 to 30. Optionally, the poly(ethylene glycol) chains may be independently capped with sulphate and/or sulphonate groups, typically with the charge being balanced by reducing the number of $X^-$ counter-ions, or (in cases where the average degree of sulphation per molecule is greater than two), introduction of $Y^+$ counter-ions, for example sodium cations.

The microfibrillated cellulose, derived from vegetables or wood, can be added to the liquid composition in an amount to effectively provide low-shear structuring and suspension of insoluble materials, while a polymeric external structurant can be add to further increase the viscosity, and provide a shear-thinning rheology profile. The liquid composition may comprise from 0.01 to 5% by weight of such a polymeric external structurant. The polymeric external structurant can be naturally derived and/or synthetic. Examples of naturally derived polymeric external structurants of use in the present invention include: hydroxyethyl cellulose, hydrophobically modified hydroxyethyl cellulose, carboxymethyl cellulose, polysaccharide derivatives and mixtures thereof. Examples of synthetic polymeric external structurants of use in the present invention include: polycarboxylates, polyacrylates, hydrophobically modified ethoxylated urethanes, hydrophobically modified non-ionic polyols and mixtures thereof. In another preferred embodiment, the polyacrylate is a copolymer of unsaturated mono- or di-carbonic acid and C1-C30 alkyl ester of the (meth) acrylic acid.

Process for Making the Liquid Composition:

The microfibrillated cellulose, derived from vegetables or wood, can be added into the liquid composition using any suitable means. For instance, the liquid composition comprising a surfactant and microfibrillated cellulose derived from vegetables or wood, can be manufactured using a process comprising the steps of: providing a structuring premix comprising microfibrillated cellulose, derived from vegetables or wood; providing a liquid premix comprising the surfactant; incorporating the structuring premix into the liquid premix using high shear mixing. Any suitable means of high shear mixing can be used, including the use of either continuous and non continuous high shear mixers. High shear mixing can be provided via a dynamic mixer or static mixer.

The structuring premix typically comprises a slurry of the microfibrillated cellulose, derived from vegetables or wood, more preferably derived from sugar beet or chicory root. The structuring premix may comprise surfactant. Suitable surfactants may be selected from the group consisting of: anionic surfactant, nonionic surfactant, cationic surfactant, and mixtures thereof. However, if present, the structuring premix preferably comprises a surfactant selected from the group consisting of: anionic surfactant, nonionic surfactant, and mixtures thereof. Nonionic surfactant is preferred.

For processes for manufacturing low water liquid compositions, the structuring premix may comprise non-aminofunctional solvent, such as propanediol. The addition of a non-aminofunctional solvent to the structuring premix improves the dispersion of the structuring premix into a low water liquid premix, which can comprise water at a level of less than 20%, preferably less than 15%, more preferably less than 10% by weight of the resultant liquid composition.

The liquid premix comprises at least one surfactant. The liquid premix typically comprises further ingredients, typically including all the ingredients that require high shear mixing. Preferably, the structuring premix of the microfibrillated cellulose is the last ingredient incorporated into the liquid composition. The structuring premix is preferably incorporated into the liquid composition using high shear mixing. Preferably, the structuring premix is incorporated into the liquid composition using average shear rates of greater than 100 s$^{-1}$, preferably from 200 s$^{-1}$ to 25,000 s$^{-1}$, more preferably from 500 s$^{-1}$ to 10,000 s$^{-1}$. The residence time of mixing is preferably less than 60, more preferably less than 25 s, more preferably less than 5 s.

The shear rate and residence time is calculated according to the methods used for the mixing device, and is usually provided by the manufacturer. For instance, for a static mixer, the average shear rate is calculated using the equation:

$$\dot{\gamma} = \frac{v_{pipe}}{D_{pipe}} * v_f^{-3/2}$$

where:
$v_f$ is the void fraction of the static mixer (provided by the supplier)
$D_{pipe}$ is the internal diameter of the pipe comprising the static mixer elements
$v_{pipe}$ is the average velocity of the fluid through a pipe having internal diameter $D_{pipe}$, calculated from the equation:

$$v_{pipe} = \frac{4Q}{\pi D_{pipe}^2}$$

Q is the volume flow rate of the fluid through the static mixer.

For a static mixer, the residence time is calculated using the equation:

$$\text{residence time} = \frac{\pi D_{pipe}^2 v_f L}{4Q}$$

where:
L is the length of the static mixer.

Methods

Method of Measuring Aspect Ratio of Microfibrillated Fibres:

The liquid composition or structuring premix is analysed using Atomic force microscopy (AFM). The sample was prepared using the following procedure: The single side polished Si wafer (<100>, 381 micron thickness, 2 nm native oxide, sourced from IDB Technologies, UK) is first cracked or cut into a piece of approximate dimensions 20×20 mm. The liquid composition or premix is applied liberally to the Si wafer, using a cotton bud (Johnson & Johnson, UK). The coated wafer is placed into a lidded poly(styrene) Petri dish (40 mm diameter, 10 mm height, Fisher Scientific, UK) and left for 20 minutes in air under ambient conditions (18° C., 40-50% RH). The Petri dish is then filled with H$_2$O(HPLC grade, Sigma-Aldrich, UK) and the sample is left in the immersed conditions for approximately 20 minutes. Following this, a cotton bud is used to remove the liquid composition or premix which has floated up away from the Si wafer surface, whilst the Si wafer was still immersed under HPLC grade H$_2$O. The Si wafer is then removed from the Petri dish and rinsed with HPLC grade H$_2$O. Subsequently, the Si wafer is dried in a fan oven at 35° C. for 10 min.

The wafer surface is then imaged as follows: The Si wafer is mounted in an AFM (NanoWizard II, JPK Instruments) and imaged in air under ambient conditions (18° C., 40-50% RH) using a rectangular Si cantilever with pyramidal tip (PPP-NCL, Windsor Scientific, UK) in Intermittent Contact Mode. The image dimensions are 40 micron by 40 micron, image height scale is set to 50 nm or less, the pixel density is set to 1024×1024, and the scan rate is set to 0.3 Hz, which corresponded to a tip velocity of 12 micron/s.

The resultant AFM image is analysed as follows: The AFM image is opened using ImageJ, version 1.46 (National Institute of Health, downloadable from: http://rsb.info.nih.gov/ij/). In the "Analyze" menu, the scale is set to the actual image size in microns, 40 µm by 40 µm. 10 fibres, which do not contact the image edge, are selected at random. Using the "freehand line" function from the ImageJ Tools menu, the selected fibres are each traced, and the length (l) and cross dimension (d) are measured (menu selections: "Plugins"/"Analyze"/"Measure and Set Label"/"Length"), and averaged across the 10 samples.

Three sets of measurements (sample preparation, AFM measurement and image analysis) are made, the results averaged.

Method of Measuring the Viscosity of the Liquid Composition:

Unless otherwise specified, the viscosity is measured using an TA instrument AR G2 rheometer (Ta Instruments US), with a cone and plate geometry having an angle of 2°, and a gap of 40 microns. The shear rate is held constant at a shear rate of 0.01 s-1, until steady state is achieved, then the viscosity is measured. The shear rate is then measured at different shear rates from 0.1 to 1000 sec-1 doing an upward shear rate sweep in 5 minutes all measurements are made at 20° C.

Method of Measuring the Yield Stress of the Liquid Composition:

The yield stress is measured using an TA instrument AR G2 rheometer (Ta Instruments US), with a cone and plate geometry having an angle of 2°, and a gap of 40 microns. A downward equilibrium shear rate sweep of from 10 s$^{-1}$ to 0.01 s$^{-1}$ is applied at 20° C., and fitted to the Herschley Buckley model: $\tau=\tau_0+K\gamma^n$, where $\tau_0$ is the shear stress, $\tau_0$ is the yield stress, and is $\gamma$ the shear rate. K and n are fitting parameters.

Method for the Determination of Soluble, Insoluble and Total Dietary Fiber:

The method for the determination of soluble, insoluble and total dietary fibre is described in McCleary et al.: *Journal of AOAC International Vol. 95, No. 3*, 2012. Determination of Insoluble, Soluble, and Total Dietary Fiber (CODEX Definition) by Enzymatic-Gravimetric Method and Liquid Chromatography: Collaborative Study.

Examples

Liquid compositions A to E, according to the present invention, were prepared as follows: Sugar beet fibres were extracted using the procedure described in U.S. Pat. No. 5,964,983, resulting in an aqueous premix of 6% by weight of microfibrillated cellulose derived from sugar beet. The remaining ingredients were blended together, using an overhead mixer. The premix comprising the microfibrillated cellulose derived from sugar beet, was then added using a ULTRA TURRAX high shear mixer, operating at 13.500 rpm for 2 min, to achieve a homogeneous dispersion of the microfibrillated cellulose, derived from sugar beet.

Comparative liquid composition F, comprising hydrogenated castor oil as the external structurant, was prepared as follows:

An aqueous premix of 4% hydrogenated castor oil, 3.2% monoethanolamine and 16% HLAS was prepared. The remaining ingredients were blended together, using an overhead mixer, to form a liquid premix. An IKA mixer, at 1.200 rpm for 1 min, was then used to blend the hydrogenated castor oil external structurant into the liquid premix, to form the finished liquid composition.

TABLE 1

Liquid compositions A to E, of the present invention, comprise microfibrillatedcellulose derived from sugar beet. Comparative liquid composition F comprises hydrogenated castor oil as the external structurant:

| | % w/w in liquid composition | | | | | |
|---|---|---|---|---|---|---|
| Component | A | B | C | D | E | F* |
| Water | 59.15 | 58.994 | 59.1781 | 59.199 | 59.1303 | 68.8 |
| Sodium Hydroxide | 5.19 | 5.11 | 5.16 | 5.18 | 5.18 | 3.72 |
| 1,2 Propanediol | 4.17 | 4.7898 | 4.384 | 4.1972 | 4.2286 | 3.17 |
| Citric Acid | 4.51 | 4.43 | 4.483 | 4.502 | 4.502 | 3.23 |
| Sodium Cumene sulphonate | 1.3 | 1.28 | 1.29 | 1.3 | 1.3 | 0.93 |
| Linear Alkylbenzene sulphonic acid[1] | 8.43 | 8.29 | 8.38 | 8.42 | 8.42 | 7.6 |
| C14-15 alkyl 7-ethoxylate | 6.17 | 6.07 | 6.14 | 6.16 | 6.16 | 4.42 |
| Calcium Choride | 0.014 | 0.014 | 0.014 | 0.014 | 0.014 | 0.01 |
| C12-18 Fatty acid | 4.39 | 4.31 | 4.36 | 4.38 | 4.38 | 3.14 |
| Diethylenetriamine penta (methylenephosphonic) acid, sodium salt[2] | 0.39 | 0.38 | 0.389 | 0.39 | 0.39 | 0.28 |
| Trans-sulphated ethoxylated hexamethylene diamine | 1.39 | 1.37 | 1.386 | 1.392 | 1.392 | 1 |
| 70 wt % C12-14 EO7 alkyl ethoxylated sulphate in water | 3.65 | 3.59 | 3.627 | 3.643 | 3.643 | 2.61 |
| Xyloglucanase[3] | — | 0.0024 | — | 0.003 | — | — |
| Mannanase[4] | — | 0.003 | — | 0.0038 | — | — |
| Protease[5] | — | 0.041 | 0.043 | — | — | — |
| Amylase 1[6] | — | 0.0059 | — | — | — | — |
| Amylase 2[7] | — | 0.0023 | — | — | — | — |
| Pectate lyase[8] | — | 0.004 | — | — | — | — |
| Cellulase[9] | — | — | — | — | 0.0035 | — |
| Sorbitol | — | 0.0834 | — | 0.0302 | — | — |
| Glycerine | — | 0.058 | — | 0.0725 | 0.0616 | — |
| Preservatives | — | 0.00411 | — | 0.0021 | — | 0.001 |
| Sodium formate | 0.41 | 0.4708 | 0.4776 | 0.4 | 0.4 | — |
| Monoethanolamine | — | — | — | — | — | 0.32 |
| Minors (perfume, antifoam silicone, solvents) | 0.49 | 0.487 | 0.4888 | 0.486 | 0.486 | 0.37 |
| Hydrogenated castor oil | — | — | — | — | — | 0.4 |
| Microfibrillated cellulose derived from sugar beet | 0.3 | 0.3 | 0.3 | 0.306 | 0.3 | — |
| Viscosity after making (at 0.01 s$^{-1}$) | 22.06 | 26.46 | 26.74 | 23.07 | 25.02 | |
| Viscosity after making (at 0.05 s$^{-1}$) | | | | | | 25.18 |
| Viscosity after making (at 1 s$^{-1}$) | 1.73 | 1.94 | 1.98 | 2.06 | 2.14 | 1.973 |
| Viscosity after 3 weeks stored at 20° C. (at 0.01 s$^{-1}$) | 28.46 | 27.73 | 33.5 | 21.03 | 24.59 | |
| Viscosity after 3 weeks stored at 20° C. (at 1 s$^{-1}$) | 1.67 | 2.27 | 2.17 | 1.86 | 1.92 | |

*Comparative
[1] produced via the HF process
[2] Dequest 2066 from Solutia Inc
[3] Whitezyme ® from Novozymes, Bagsvaerd, Denmark. This is a variant of a family 44 glycosyl hydrolase
[4] Mannaway ® from Novozymes, Bagsvaerd, Denmark
[5] Purafect ® Prime from DuPont Industrial Biosciences, Palo Alto, U.S.A.
[6] Natalase ® from Novozymes, Bagsvaerd, Denmark
[7] Termamyl ® from Novozymes, Bagsvaerd, Denmark
[8] x-Pect ® from Novozymes, Bagsvaerd, Denmark
[9] Carezyme ® from Novozymes, Bagsvaerd, Denmark From comparing liquid compositions A to E with comparative composition F, it can be seen that liquid compositions comprising as an external structurant, microfibrillated cellulose, derived from sugar beet, have a similar viscosity profile to liquid compositions comprising hydrogenated castor oil as the external structurant.

In addition, by comparing the viscosity profile of liquid compositions B to E, aged for 3 weeks at room temperature, with the viscosity profile of liquid composition A, it can be seen that both the low and high shear viscosity of the liquid compositions are unaffected by the presence of enzymes such as Xyloglucanase, Protease, Cellulase, and the like.

TABLE 2

Liquid compositions comprising microfiber cellulose derived from sugar beet pulp or chicory root:

| Ingredient | Liquid composition G wt % | Liquid composition H wt % |
|---|---|---|
| Linear Alkylbenzene sulphonic acid | 7.5 | 10.5 |
| C12-14 alkyl ethoxy 3 sulphate Na salt | 2.6 | — |
| C12-14 alkyl ethoxy 3 sulphate MEA salt | — | 8.5 |
| C12-14 alkyl 7-ethoxylate | 0.4 | 7.6 |
| C14-15 alkyl 7-ethoxylate | 4.4 | — |
| C12-18 Fatty acid | 3.1 | 8 |
| Sodium Cumene sulphonate | 0.9 | — |
| Citric acid | 3.2 | 2.8 |
| Ethoxysulfated Hexamethylene Diamine Dimethyl Quat | 1 | 2.1 |
| Soil Suspending Alkoxylated Polyalkylenimine Polymer[2] | 0.4 | — |
| PEG-PVAc Polymer[3] | 0.5 | 0.8 |
| Di Ethylene Triamine Penta (Methylene Phosphonic acid, Na salt) | 0.3 | — |
| Hydroxyethane diphosphonic acid | — | 1.5 |
| Fluorescent Whitening Agent | 0.1 | 0.3 |
| 1,2 Propanediol | 3.9 | 7.5 |
| Diethylene Glycol | — | 3.5 |
| Sodium Formate | 0.4 | 0.4 |
| Microfibrillated cellulose derived from sugar beet pulp | 0.3 | — |
| Microfibrillated cellulose derived from chicory root | — | 0.5 |
| Perfume | 0.9 | 1.7 |
| Sodium Hydroxide | To pH 8.4 | — |
| Monoethanolamine | 0.3 | To pH 8.1 |
| Protease enzyme | 0.4 | 0.7 |
| Amylase enzyme | — | 0.7 |
| Mannanase enzyme | 0.1 | 0.2 |
| Xyloglucanase enzyme | — | 0.1 |
| Pectate lyase | 0.1 | — |
| Water and minors (antifoam, aesthetics, . . .) | To 100 parts | |

Alternatively, the aqueous structuring premixes, according to the invention, can be added to low water unstructured treatment compositions, to form structured low water treatment compositions, as described below.

TABLE 3

Low water liquid compositions comprising microfiber cellulose derived from sugar beet pulp or chicory root:

| Ingredient | Liquid composition E wt % | Liquid composition F wt % | Liquid composition G wt % |
|---|---|---|---|
| Linear Alkylbenzene sulphonic acid[1] | 15 | 17 | 19 |
| C12-14 alkyl ethoxy 3 sulphonic acid | 7 | 8 | — |
| C12-15 alkyl ethoxy 2 sulphonic acid | — | — | 9 |
| C14-15 alkyl 7-ethoxylate | — | 14 | — |
| C12-14 alkyl 7-ethoxylate | 12 | — | — |
| C12-14 alkyl-9-ethoxylate | — | — | 15 |
| C12-18 Fatty acid | 15 | 17 | 5 |
| Citric acid | 0.7 | 0.5 | 0.8 |
| Polydimethylsilicone | — | 3 | — |
| Soil Suspending Alkoxylated Polyalkylenimine Polymer[2] | 4 | — | 7 |
| Hydroxyethane diphosphonic acid | 1.2 | — | — |
| Diethylenetriamine Pentaacetic acid | — | — | 0.6 |
| Ethylenediaminediscuccinic acid | — | — | 0.6 |
| Fluorescent Whitening Agent | 0.2 | 0.4 | 0.2 |
| 1,2 Propanediol | 16 | 12 | 14 |
| Glycerol | 6 | 8 | 5 |
| Diethyleneglycol | — | — | 2 |
| Microfibrillated cellulose derived from sugar beet pulp | 0.15 | — | — |
| Microfibrillated cellulose derived from chicory root | — | 0.25 | 0.1 |
| Perfume | 2.0 | 1.5 | 1.7 |
| Perfume microcapsule | — | 0.5 | — |
| Monoethanolamine | Up to pH 8 | Up to pH 8 | Up to pH 8 |
| Protease enzyme | 0.05 | 0.075 | 0.12 |
| Amylase enzyme | 0.005 | — | 0.01 |
| Mannanase enzyme | 0.01 | — | 0.005 |
| xyloglucanase | — | — | 0.005 |
| Water and minors (antifoam, aesthetics, stabilizers etc.) | To 100 parts | To 100 parts | To 100 parts |

The resultant low water treatment compositions can be encapsulated in water-soluble film, to form water-soluble unit-dose articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid composition comprising:
   a) surfactant,
   b) microfibrillated cellulose derived from sugar beet; and
   c) enzymes selected from the group consisting of: cellulases, endoglucanase with activity towards xyloglucan, and mixtures thereof.

2. The composition according to claim 1, wherein the surfactant is selected from the group consisting of: anionic surfactant, nonionic surfactant, cationic surfactant, and mixtures thereof.

3. The composition according to claim 1, wherein the composition comprises from about 0.5% to about 40 wt % of the surfactant.

4. The composition according to claim 1, wherein the microfibrillated cellulose has an aspect ratio (l/d) of from about 50 to about 200,000.

5. The composition according to claim 1, wherein the microfibrillated cellulose is derived from sugar beet and comprises less than about 10% soluble fibre as a percentage of total fibre.

6. The composition according to claim 1, wherein the composition comprises from about 0.05 to about 10 wt % of the microfibrillated cellulose.

7. The composition according to claim 1, wherein the composition comprises sufficient microfibrillated cellulose to provide a yield stress of greater than about 0.005 Pa.

8. The composition according to claim 1, wherein the composition further comprises a suspended insoluble material.

9. A liquid composition comprising:
   a) surfactant, and
   b) microfibrillated cellulose derived from sugar beet,
   wherein the composition further comprises a water-soluble polymer.

10. The composition according to claim 9, wherein the water-soluble polymer is selected from carboxylate polymers, polyethylene glycol polymers, polyester soil release polymers, amine polymers, cellulosic polymers, dye transfer inhibition polymers, dye lock polymers, hexamethylenediamine derivative polymers, and mixtures thereof.

11. A process to manufacture a liquid composition comprising a surfactant, enzymes, and microfibrillated cellulose, the process comprising the steps of:
   a) providing a structuring premix comprising microfibrillated cellulose, wherein the microfibrillated cellulose is derived from sugar beet;
   b) providing a liquid premix comprising the surfactant, wherein said liquid premix further comprises enzymes selected from the group consisting of: cellulases, endoglucanase with activity towards xyloglucan, and mixtures thereof; and
   c) incorporating the structuring premix into the liquid premix using high shear mixing.

12. A process according to claim 11, wherein the structuring premix comprises a surfactant.

13. A composition according to claim 10, wherein the water-soluble polymer comprises a soil release polymer, wherein the soil release polymer comprises terephthalate polymers.

14. A composition according to claim 1, wherein the composition comprises from 0.15 wt % to 2 wt % of the microfibrillated cellulose.

15. A composition according to claim 1, wherein the composition further comprises an enzyme, wherein the enzyme comprises lipase.

16. A composition according to claim 8, wherein the suspended insoluble material comprises microcapsules, wherein the microcapsules comprise a microcapsule core and a microcapsule wall that surrounds the microcapsule core.

17. A composition according to claim 16, wherein the microcapsules are perfume microcapsules.

* * * * *